United States Patent [19]
Kao

[11] Patent Number: 6,090,590
[45] Date of Patent: Jul. 18, 2000

[54] REDUCING NONTEMPLATED 3' NUCLEOTIDE ADDITION TO POLYNUCLEOTIDE TRANSCRIPTS

[75] Inventor: C. Cheng Kao, Bloomington, Ind.

[73] Assignees: The Regents of the University of California, Oakland, Calif.; Advanced Research and Technology, Inc., Indianapolis, Ind.

[21] Appl. No.: 09/371,487

[22] Filed: Aug. 10, 1999

[51] Int. Cl.[7] .............................. C12P 19/34; C12Q 1/68; C07H 21/02; C07H 21/04
[52] U.S. Cl. ......................... 435/91.1; 435/6; 435/91.2; 536/23.1; 536/23.72; 536/24.3; 536/24.33
[58] Field of Search ............................. 435/6, 91.1, 91.2, 435/91.51, 91.33, 91.32, 183; 536/22.1, 23.1, 23.72, 24.3, 24.33, 25.3; 436/94

[56] References Cited

PUBLICATIONS

Moran et al., Non–hydrogen bonding 'terminator' nucleosides increase the 3'–end homogeneity of enzymatic RNA and DNA synthesis. Nucl. Acids. Res. 24, 2044–2052, 1996.
Tunitskaya et al., Substrate properties of C'–methyl derivatives in T7 RNA polymerase reactions. Evidence of N–type NTP conformation. FEBS Lett. 400, 263–266, 1997.

*Primary Examiner*—Bradley L. Sisson
*Assistant Examiner*—Frank Lu
*Attorney, Agent, or Firm*—Richard Aron Osman

[57] ABSTRACT

Non-template 3' nucleotide addition to a transcript is reduced by transcribing a transcript from a template comprising an ultimate and/or penultimate 5' ribose having a C'2 substituent such as methoxy, which reduces non-template 3' nucleotide addition to the transcript. The methods are shown to be applicable to a wide variety of polymerases, including Taq, T7 RNA polymerase, etc.

17 Claims, No Drawings

REDUCING NONTEMPLATED 3' NUCLEOTIDE ADDITION TO POLYNUCLEOTIDE TRANSCRIPTS

The research carried out in the subject application was supported in part by NIH Grant GM10840, DOE Grant DE-FG03-86ER60406, NSF Grant MCB9507344 and USDA Grant 9702126. The government may have rights in any patent issuing on this application.

INTRODUCTION

1. Field of the Invention

The field of the invention is reducing nontemplated '3 nucleotide addition during enzymatic synthesis of nucleic acids.

2. Background of the Invention

In vitro transcription is widely used to produce polynucleotide copies for a wide variety of applications, including structural and biochemical studies and therapeutics. Despite its usefulness, a number of undesired reactions increase the complexity of the polymerase products and necessitate careful purification. These reactions include the synthesis of oligonucleotides aborted during the initiation of transcription, polymerase slippage, the use of alternative template initiation sites, and the addition of one or more nontemplated nucleotides at the 3' termini of nascent transcripts (hence forth called the N+1 activity). N+1 activity can be a major contributing factor to heterogeneity in transcription products (Milligan et al., 1987, Nucl. Acid Res. 15:8783–8798; Krupp, 1988, Gene 72: 75–89) and has been found to be associated with the popular T7 RNA polymerase. The synthesis of DNA by the Taq polymerase also has N+1 activity.

The heterogeneity at the 3' ends of transcripts generated by polymerases in vitro can have detrimental effects in a number of applications. In the production of infectious viral transcripts, 3' heterogeneity may reduce the synthesis by viral RNA replicase (Sun et al., 1996, Virology 226:1–12.), or reduce the infectivity of the RNA (Murphy & Park, 1997, Virology 232: 145–157). In biochemical and structural analyses of RNA structures, 3' heterogeneity may result in additional signals that complicate the interpretation of results and may prevent the effective crystallization of the RNA needed for X-ray crystallography (Price et al., 1995, J. Mol. Biol. 249: 398–408.). Previously, one commonly used strategy to generate a homogeneous RNA sample of less than 50-nts is to perform denaturing gel electrophoresis and to excise and elute the desired band (Wyatt et al., 1991, BioTechniques 11:764–769.). For RNAs longer than 50-nts, where it is difficult to separate the N+1 RNA from the desired RNA by gel electrophoresis, the transcript can be expressed with a cis-acting ribozyme sequence that will cleave at the desired positions (Price et al., 1995, supra), or by use of a mutant T7 RNA polymerase that is defective in its initiation rate (Gardener et al., 1997, Biochemistry 36:2908–18.). Alternatively, Moran et al., (1996, Nucl. Acids Res. 24: 2044–2052) demonstrated that DNA templates containing nucleoside with base analogs that cannot form hydrogen bonds with the substrate nucleotide can induce the termination of transcription prior to the nucleoside analog. However, these analogs are not widely available, may alter transcriptional fidelity, and often leave a significant amount of N+1 activity.

We disclose here that modification of either the penultimate and/or ultimate nucleotide at the 5' terminus of template DNA or RNA with functional groups at the ribose C'2 position significantly reduces N+1 activity by polymerases and can increase the abundance of the desired transcript. Our ability to generate less complex transcription products permits more rapid RNA purification such as by high-pressure liquid chromatography.

SUMMARY OF THE INVENTION

The invention provides methods and compositions for reducing non-template 3' nucleotide addition to a transcript, comprising the step of transcribing a transcript from a template comprising an ultimate and/or penultimate 5' ribose having a C'2 substituent which reduces non-template 3' nucleotide addition to the transcript. The methods are shown to be applicable to a wide variety of polymerases, including Taq, Klenow, T7 RNA polymerase, HIV reverse transcriptase, $3D^{pol}$ RNA-dependent RNA polymerase, etc. The polynucleotides generally comprise RNA and/or DNA; the template may be single or double stranded, while the transcript is single stranded; and the substituent comprises a moiety conveniently substituted for the native hydroxyl at C'2, such as methoxy, ethoxy, sulfoxy, halogenated moieties, etc.

DETAILED DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or, polynucleotide sequences are understood to encompass opposite strands as well as alternative backbones and "ribose" is the generic cylcopentose component of nucleic acids and includes deoxyribose.

In studies of RNA synthesis by a viral RNA-dependent RNA polymerase, we noticed that nontemplated nucleotide addition on the nascent RNA was decreased when the 5' terminus of the template was modified with deoxyribonucleotides (Siegel et al., 1999, J Virol 73(8):6424–6429). We subsequently determined that a DNA template containing nucleotide analogs at the 5' terminus would similarly affect RNA synthesis by the T7 RNA polymerase and have now extended these findings to a wide range of templates, transcripts and polymerases. Accordingly, we show how non-template 3' nucleotide addition to a transcript can be reduced by employing a template comprising an ultimate and/or penultimate 5' ribose having a terminator substituent at the C'2 position.

As used herein, "template" refers to a polynucleotide to be copied; "transcript" refers to the nascent polynucleotide made by copying the template with a polymerase. These polynucleotides generally comprises DNA and/or RNA or combinations and/or heterohybrids thereof, though other nucleotide analogs may also be incorporated. Reducing non-template nucleotide addition means relative to a transcript made from an otherwise identical template polynucleotide but without the C'2 terminator substituent. Reductions effected are generally at least 50%, preferably at least 75%, more preferably at least 95%.

A wide variety of C'2 terminator substituents may be used. Nucleotide analogs having preferred substituents are commercially available and inexpensive to incorporate during the chemical synthesis of DNA and provide an unchanged base, so the identity of the nucleotide incorporated into the nascent RNA is unaffected. The suitability of a given substituent depends on the substituent, polymerase, template and reaction conditions, and is readily determined empirically as shown below. For example, a methoxy substituent was found particularly effective with T7 RNA polymerase transcription of S5 under the conditions described in the Examples section below, while fluorine and amine substituents were not. Table 1 provides results showing the applicability of the methods to a wide range of templates, transcripts, terminator substituents and polymerases.

Table 1. Reduction of non-template 3' nucleotide addition by Taq, Klenow, T7 RNA polymerase (T7 Pol), HIV reverse transcriptase (HIV-RT) and 3D$^{pol}$ RNA-dependent RNA polymerase (3D$^{pol}$) using various DNA and RNA templates including S5 (below), BMV (Siegel et al., 1999, supra), RBSb, Rib1, U1, U2 (Moran et al., 1996, supra), et al.

| Template | Transcript | C'2 substituent | Polymerase | Reduction |
|---|---|---|---|---|
| DNA | RNA | methoxy | T7 Pol | >50% |
| DNA | RNA | ethoxy | T7 Pol | >50% |
| DNA | RNA | sulfoxy | T7 Pol | >50% |
| DNA | DNA | methoxy | Taq | >50% |
| DNA | DNA | F | Taq | >50% |
| DNA | DNA | OCHCl$_3$ | Taq | >50% |
| DNA | DNA | methoxy | Klenow | >50% |
| DNA | DNA | Cl | Klenow | >50% |
| DNA | DNA | sulfoxy | Klenow | >50% |
| RNA | DNA | methoxy | HIV-RT | >50% |
| RNA | DNA | ethoxy | HIV-RT | >50% |
| RNA | DNA | I | HIV-RT | >50% |
| RNA | RNA | methoxy | 3D$^{pol}$ | >50% |
| RNA | RNA | ethoxy | 3D$^{pol}$ | >50% |
| RNA | RNA | sulfoxy | 3D$^{pol}$ | >50% |

EXAMPLES

Transcription from DNA template containing ribose 2'-methoxy analogs. As an initial test, we used a DNA named S5 which should encode a 22-nt RNA within P5 of the *Tetrahymena thermophila* group I intron. For nomenclature, DNA templates with modified (ribose at the C2' position with a methoxy moiety) 5' terminal nucleotide (s) are denoted with one or two asterisks following the name shared with the unmodified template. In a typical transcription reaction as performed by the protocol of Milligan et al. (1987, supra), the DNA template, S5, directed production of a 23-nt N+1 RNA at amounts between 50 to 200% of the amount of the desired 22-nt RNA. When S5 was used in the transcription reaction, we noted that the amount of N+1 product made was not only significantly reduced, but the 22-nt transcript was reproducibly more abundant than that from S5. In more careful analysis, the 22-nt transcript from S5 was reproducibly increased two to three fold compared to amounts made from S5.

The above observation prompted us to investigate whether either or both modified guanylates in S5** were required to reduce the N+1 activity. DNA templates that contained one guanosine ribose 2'-methoxy moiety at the 5'-terminus (S5$^{G}$*), or at the penultimate position (S5*$^{G}$), were made, and their transcription products compared with those from S5 and S5. Template S5 and S5*$^{G}$ significantly reduced the N+1 transcript while S5$^{G}$* did not. Therefore, modification of the penultimate position is the most important in reducing N+1 activity. In addition to the N+1 product, a minute amount of N+2 RNA was observed in overloaded gels. The transcripts from S5** had a reduction of the N+2 RNA. Therefore we routinely used DNA templates modified in the two terminal nucleotides in the following examples.

To determine whether the modified template would affect the identity of the nucleotide incorporated into the RNA, we purified the 22-nt RNA generated from a 30 mL transcription using template S5 and a 10 mL transcription which used S5 and compared their nuclear magnetic resonance (NMR) spectra. Since the nucleotides of interest are at the 3' terminus of the respective RNAs, and the imino protons of the corresponding basepair cannot be observed due to fast exchange with the solvent, we examined the nonexchangeable ribose H1' and H5 protons, whose chemical shifts are affected by the identity of the base. We previously determined that the terminal cytidylate in the RNA has an H1' peak at 5.75 ppm and a H5 peak at 5.6 ppm. We observed these peaks at the same chemical shifts when using RNA transcribed from either S5 and S5. In addition, all other peaks from the two RNAs corresponded exactly. Finally, the H6 proton of cytidine 22, was found at 7.66 ppm in both samples, further confirming that modifications in S5** did not alter the sequence of the transcription product.

Four additional DNA templates that should direct the synthesis of RNAs from 27 to 64 nts were examined. The modified DNAs were named P1, VΨ, M5-54, and M5-64, and their 5' terminal nucleotides were, respectively, 5'GA3', 5'AT3', 5'GG3' and 5'GG 3'. The unmodified versions of all four DNAs generated significant amounts of the respective N+1 products while the modified DNAs did not. We also produced four additional RNAs from modified templates that had significantly reduced N+1 RNAs. Transcription reactions using P1 and VΨ generated RNAs that were either one or two nucleotides less than full-length. The modified DNA templates did not significantly affect the abundance of these truncated RNAs.

Transcripts longer than 50 nts are difficult to purify away from their associated N+1 RNAs even after extensive preparative gel electrophoresis. This has led to contamination of the desired transcripts that can complicate spectroscopic and biochemical analyses of RNAs. For example, Wu and Tinoco (1998, *Proc. Natl. Acad. Sci.* 95: 11555–11560) observed in a 56-nt RNA three additional imino signals associated with the last three basepairs of the N+1 RNA. In one-dimensional imino spectrum of the 56-nt RNA, the peak at 12.58 ppm (labeled G191$^+$), and the shoulder at 13.2 ppm (labeled G131$^+$), were tentatively assigned to the N+1 RNA because it was not possible to separate the N+1 RNA from the 56-nt RNA. To examine whether transcripts purified from the modified template could remove the confounding signals, we purified the transcripts from a modified template encoding the 56-nt sequence used by Wu and Tinoco (1988, supra) and performed 1-D imino spectra analysis. The transcript from the modified template, M5-56** lacked the G191$^+$ signal, was significantly enhanced in the signal for G131 and G191, and did not have the extra peak shoulder associated with G131$^+$. All other peaks were unaffected, demonstrating that the nucleotide sequence produced from modified template M5-56 was identical to the expected sequence.

Transcription from double-stranded templates. RNAs of less than a 100 nt can be transcribed from chemically synthesized DNA templates where only the promoter sequence is double-stranded (Milligan et al., 1987, supra). However, chemical DNA synthesis is impractical for transcription of longer RNAs, and the double-stranded templates generated by polymerase chain reaction (PCR) are more suitable (Ausubel et al., 1995, *Current Protocols in Molecular Biology*. Wiley, New York.). To determine whether the ribose 2'-methoxy modifications could potentially affect transcription from double-stranded DNA templates, we used Taq DNA polymerase and dNTPs to extend the oligonucleotide containing the T7 promoter sequence hybridized to DNA S5 and VΨ, or to S5 and VTΨ. Half of the extension products were analyzed by gel electrophoresis to confirm that duplex DNAs were formed. Double-stranded S5 and VΨ again directed products that lacked the N+1 RNAs while unmodified double-stranded S5 and VΨ each produced significant amounts of N+1 products. In PCR products, a DNA primer generates the 5' terminus of the template strand for transcription. The above results with double-stranded templates indicate that DNAs amplified by PCR using modified primers will also reduce N+1 activity.

Molecular manipulations. The majority of the oligonucleotides used in this study were synthesized using an Applied Biosystem DNA synthesizer (model 381A) with reagents purchased from Glen Research. Some oligonucleotides were purchased from Operon Technologies (Alameda, Calif.). Transcriptions used the conditions described in Wyatt et al., 1991, supra. Briefly, the template DNA strand and the T7 promoter DNA strand were purified via denaturing polyacrylamide gel electrophoresis and then adjusted to 8 μM. One μL of each DNA was used in a 20 μL transcription reaction containing a final concentration of 40 mM Tris, pH 8.1, 1 mM spermidine, 0.01% Triton X-100(Union Carbide), 80 mg/reaction of polyethylene glycol 8000, and 4 mM of each NTP. The T7 RNA polymerase used was purified using the protocol of Grodberg and Dunn (1988) *J Bacteriol.* 170:1245–1253.

Double-stranded DNA templates were synthesized using Taq DNA polymerase in the buffer described in Ausubel et al. (1995). The reaction was performed in two cycles as follows: the reaction was heated to 90° C. and cooled to 45° C. to allow annealing of the oligonucleotides. Taq polymerase was then added as the reaction was incubated for 30 min at 70° C. After the extension the reaction was extracted with a 1:1 mixture of phenol-chloroform and then precipitated with 3 vol of ethanol, washed with 70% ethanol and dried prior to transcription. The RNAs were visualized following staining with Toluidine Blue as described by the manufacturer (Boehringer Mannheim Inc.)

Nuclear magnetic resonance spectroscopy. RNA transcripts used for NMR samples were prepared as described by Wyatt et al., 1991, supra. NMR spectroscopy was performed on a Bruker AMX-600 or a Bruker DRX-500 (Billerica, Mass.) at field strength of 600.14 MHz and 500.13 MHz respectively. All samples were dissolved in a phosphate buffer containing 90% H2O and 10% D2O. Spectra for the RNAs generated from S5 (2.9 mM sample) and S5 (2.7 mM sample) were taken at 30° C. with 16384 complex points in 64 scans. The proton carrier frequency was set at 4.72 ppm and the maximum for excitation was set at 7.7 ppm. For the spectra of RNAs transcribed from M5-56 and M5-56 (each at 1 mM), the spectra were recorded at 10° C. using a 1–1 pulse sequence for water suppression (Plateau & Gueron, 1982, *J Am. Chem. Soc.* 104: 7311–7312; Hore, 1983 *J. Magnetic Resonance* 55: 283–300.). The carrier frequency was centered on the water resonance frequency and the excitation profile was maximized at 12 ppm.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for reducing non-templated 3' nucleotide addition to a transcript, comprising the step of transcribing wit a polymerase a transcript from a template comprising an ultimate or penultimate 5' ribose having a C'2 terminator substituent which reduces non-template 3' nucleotide addition to the transcript by at least 50%, relative to an otherwise identical natural template, yet permits the template to function as a substrate of the polymerase.

2. A method according to claim 1, wherein the template is a DNA and the transcript is a RNA.

3. A method according to claim 1, wherein the template is a DNA and the transcript is a DNA.

4. A method according to claim 1, wherein the template is a RNA and the transcript is a RNA.

5. A method according to claim 1, wherein the template is a RNA and the transcript is a DNA.

6. A method according to claim 1, wherein the template comprises a penultimate ribose having a C'2 terminator substituent which reduces non-template 3' nucleotide addition to the transcript.

7. A method according to claim 1, wherein the template comprises a penultimate and an ultimate ribose having a C'2 terminator substituent which reduces non-template 3' nucleotide addition to the transcript.

8. A method according to claim 1, wherein the template is at least partially double stranded.

9. A method according to claim 1, wherein the reduction is at least 75%.

10. A method according to claim 1, wherein the reduction is at least 95%.

11. A method according to claim 1, wherein the terminator substituent is methoxy, ethoxy, sulfoxy or halogen.

12. A method according to claim 1, wherein the terminator substituent is methoxy.

13. A method according to claim 1, wherein the transcribing step is effected by a polymerase selected from Taq, Klenow, T7 RNA polymerase, HIV reverse transcriptase and 3D$^{pol}$ RNA-dependent RNA polymerase.

14. A method according to claim 1, wherein the transcribing step is effected by a T7 polymerase.

15. A method according to claim 1, wherein the non-template 3' nucleotide addition is N+1 addition.

16. A method according to claim 1, wherein the non-template 3' nucleotide addition is N+2 addition.

17. A method for reducing non-template 3' nucleotide addition to a transcript, comprising the step of transcribing a transcript from a template comprising an ultimate or penultimate 5' ribose having a C'2 substituent which reduces non-template 3' nucleotide addition to the transcript, relative to an otherwise identical natural template, wherein the template is a DNA and the transcript is a RNA, wherein template comprises a penultimate ribose having a C'2 substituent which reduces non-template 3' nucleotide addition to the transcript, wherein the reduction is at least 50%, wherein the substitute is methoxy, and wherein the non-template 3'nucleotide addition is N+1 addition.

\* \* \* \* \*